United States Patent [19]

Calmanovici

[11] Patent Number: 4,644,959
[45] Date of Patent: Feb. 24, 1987

[54] METHOD OF FUNCTIONAL ASSESSMENT OF CANCER HUMORAL FACTORS

[76] Inventor: Sergiu Calmanovici, 127 Allenby Street, Haifa 35 513, Israel

[21] Appl. No.: 667,252

[22] Filed: Nov. 1, 1984

[30] Foreign Application Priority Data

Apr. 12, 1984 [IL] Israel ............................... 71537

[51] Int. Cl.⁴ .............................................. A61B 5/05
[52] U.S. Cl. .................................................... 128/733
[58] Field of Search ............................. 128/635, 733

[56] References Cited

U.S. PATENT DOCUMENTS

3,364,929  1/1968  Ide et al. ............................ 128/733
4,148,303  4/1979  Cohen ................................. 128/733
4,291,703  9/1981  Sveringhaus et al. .............. 128/733

*Primary Examiner*—William E. Kamm
*Attorney, Agent, or Firm*—Browdy and Neimark

[57] ABSTRACT

Improved cancer diagnostics are achieved by initially stimulating the neuromuscular junction of an amphibian to inactivate same synatic units and lower the functional safety margin of the other synaptic units. The amphibian is then injected with the serum of a cancer patient and further stimulated to elicit an cancer electromyographically evoked pattern. The pattern may be used as a diagnostic aid or for the detection and isolation of cancer humoral products having biological activity.

7 Claims, 15 Drawing Figures

METHOD OF FUNCTIONAL ASSESSMENT OF CANCER HUMORAL FACTORS

FIELD OF THE INVENTION

This invention relates to cancer diagnostics and more specifically to cancer diagnostics employing the analysis of humoral factors.

BACKGROUND OF THE INVENTION

Detection of specific changes in the blood of cancer patients is considered to be of great practical importance. Besides the theoretical interest raised by this question it represents also a hope for finding a paraclinical test of practical usefulness in the detection of the cancer disease as early as possible.

In the last decades a number of findings provided by various fields of medicine have been proposed as being indicative of the presence of the neoplastic condition. These data are related to qualitative and quantitative enzymatic changes which appear in the blood of cancer patients, such as variations in the titers of histaminase, lactic dehydrogenase or seric aldolase, or tumor specific or organ specific findings such as acid phosphatase, alkaline phosphatase or thyroid carcinoma products. All these various data have in common the postulate of a basic difference between the metabolism of the normal and the malignant cell, which difference is enzymatically detectable.

Other biological research has led to the finding, in the blood of cancer patients, of pathological proteins such as alpha 1 and alpha 2, and other paraproteins have also been identified. Recently, advances in immunology and refinements in immunodiagnostic techniques have led to the discovery of a large range of cancer markers, the best known of them being the oncofetal antigens (carcino embryonic antigen—CEA, alpha feto protein, AFP, pancreatic oncofetal antigen, beta oncofetal antigen,) or the series of placental antigens of the ectopic hormones recently discovered, and also the oncogenic viruses.

However, the practical value of these markers for diagnostic purposes is limited by the great number of false positive and false negative results which accompany the blood investigation performed on cancer patients and control groups. In spite of their multiplicity, none of the markers has been able to provide a satisfactory answer to the need for a cancer diagnostic test and a certain amount of reliable information may be obtained only by the use of a battery of biochemical tests.

In spite of the great diversity of the pathological factors found in the blood of cancer patients, their identification is made by means of biochemical or immunochemical methods only, and in no case is the functional value of the pathological products assessed. Actually, in spite of the very well-known clinical effects of the cancerous intoxication on the whole body (the paraneoplastic syndrome), no laboratory test has yet been found in which the humoral changes of cancer are checked by the functional effects induced on other living tissues.

SUMMARY OF INVENTION

It is an object of this invention to present a novel method of diagnosing cancer.

It is another object of this invention to obtain reliable information concerning the presence and effects of cancer humoral factor.

These and other objects are achieved by the assessment of the functional perturbations produced in a living animal model, in this case the amphibia with intact metabolism, by the use of the serum of the cancerous patient to be checked and an original method of neurostimulation.

Neurological studies performed thirty years ago on the remote neurological effects of cancer in humans led to the emg identification of the paraneoplastic condition known as Eaton-Lambert Syndrome (E L Sy). This discovery postulates a humoral toxic cancer product active in only a limited category of cancer cases. No other neurophysiological advancements have been recorded since the E L Sy description.

The present invention deals with the experimental production of a paraneoplastic syndrome in amphibians and the emg pattern which ensues. The emg pattern is unique among other emg expressions known to date. A preliminary condition is the encounter between the particular spatial arrangement of amphibian muscle innervation and a temporal coordinate represented by the sequential activation of the synaptic units. Ultimately, the Cancer Electromyographically Evoked Pattern (CEEP) is due to a partial neuromuscular transmission defect whose electrical expression is determined by the philogenetic development of the muscle innervation. The investigation of the CEEP with multielectrodes (14 leads) displays electromyographically the dynamics of the physiological events. The CEEP discovery establishes a philogenetic approach for emg assessment in non-human species. The neuromuscular and junction in this model proves to be a sensitive detector for the bioassay of foreign substances.

By the original method of neurostimulation presented by this invention, the neurotoxic effects of various cancer humoral factors are made apparent. The original method of neurostimulation includes stimulating the neuromuscular junction of a vertebrate, especially an amphibian, at a frequency and intensity sufficient to lower the functional safety margin of some synaptic units and inactivate others. After this stimulation has been carried out, the serum of a suspected cancer patient is injected into the test animal while stimulation is continued. After the serum is injected, the frequency, intensity and duration of stimulation is varied to obtain a cancer evoked electromyographical pattern which is recorded and compared with normal electromyographical patterns to diagnose the presence or absence of cancer.

BRIEF DESCRIPTION OF THE DRAWINGS

FIG. 15—is a flow chart of the preferred method for carrying out the process of the present invention.

DETAILED DESCRIPTION OF THE INVENTION

Figure 1:
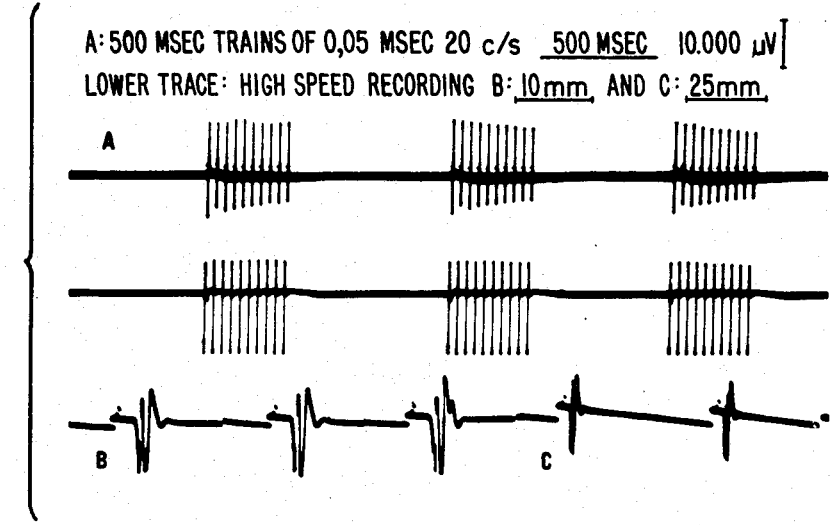
FIG. 1—Normal EMG response of frog's gastrocnemius muscle at repetitive train stimulation.

FIG. 1 shows an electromyogram (EMG) of a normal frog's right and left gastrocnemius. Note the equal sized polyphasic action potential (AP) trains.

Figure 2:
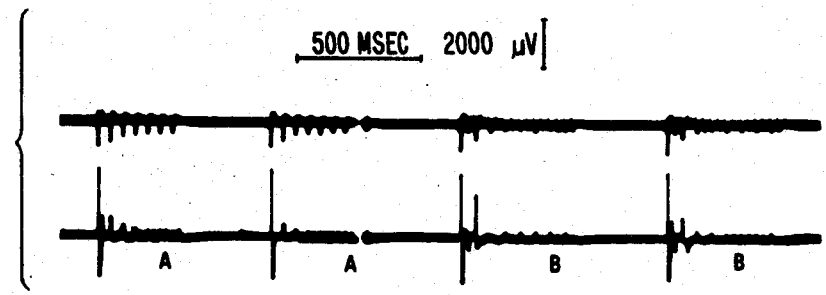
FIG. 2—CEEP of various morphology aspects produced by serum of gastric cancer patient.

FIG. 2 shows the EMG of the left and right gastrocnemius muscle of a toad after injection with the serum of a 60 year old male gastric cancer patient. The section labeled "A" shows 500 msec trains of 0.05 sec and the section labeled "B" shows 700 msec trains of 0.05 msec. Note in "A", the different CEEP in the two leads. Note in "B" that the increase in the length of the train brings about potentiation of the pattern on the upper lead.

Figure 3:
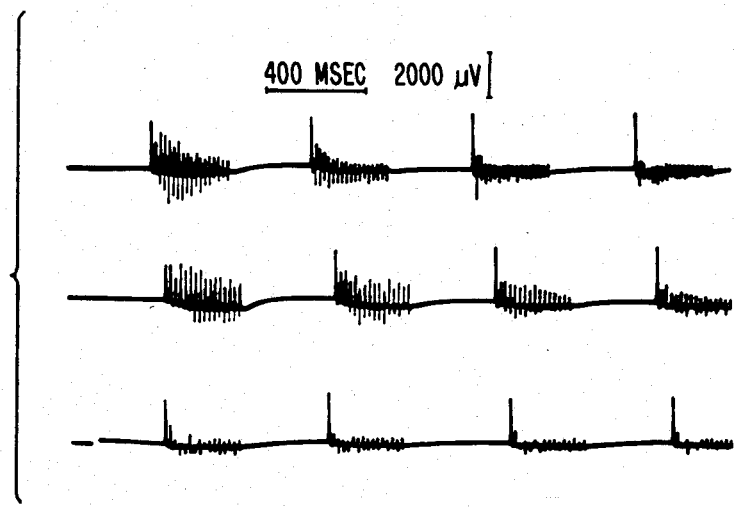
FIG. 3—Very stable CEEP produced by serum of patient with acute lymphatic leukemia.

FIG. 3 shows the EMG of the frog left gastrocnemius after injection with the serum of a patient having acute lymphatic leukemia. The EMG shows 500 msec trains of 0.05 msec at 30 c/s stimulation. Note the rapid elicitation of a high resolution CEEP and high-voltage cancer electromyographical accident (Ca E Ac) (also called "First Cancer Accident"). The pattern persists indefinitely (lower trace).

Figure 4:
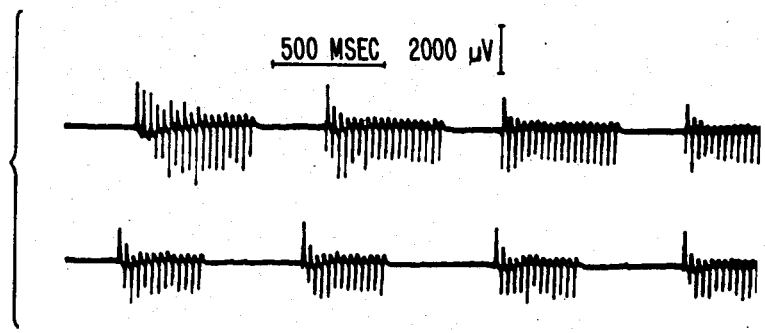
FIG. 4—Monophasic phase opposition of CEEP.

FIG. 4 shows the EMG of a frog gastrocnemius after injection with the serum of a 45 year old man with osteo sarcoma. 700 msec (upper trace) and 500 msec (lower trace) trains of 0.05 at 26 c/s stimulation are shown. Note on the upper trace the biphasic Ca E Ac and the high-voltage AP train. Note on the lower trace the monophasic phase opposition first action potential (FAP). The overcharge (longer trains) induces an EMG activation.

Figure 5:
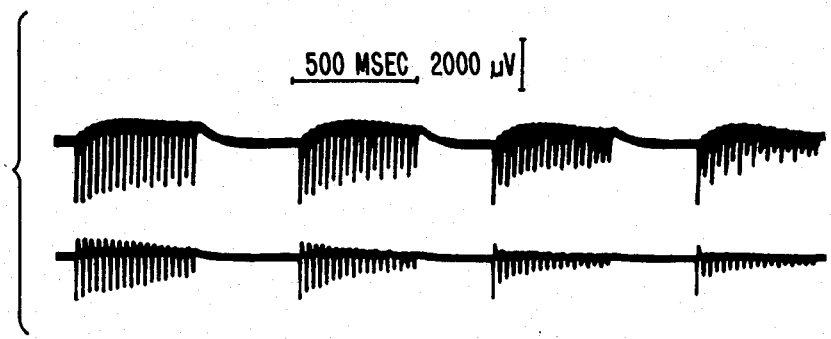
FIG. 5—Elicitation of CEEP in a case of prostatic metastatic cancer by sawtooth phenomena.

FIG. 5 shows the EMG of a frog left gastrocnemius after injection with the serum of a prostate metastatic cancer patient 700 msec trains of 0.05 msec are shown. Note the elicitation of the CEEP by sawtooth phenomenon. Also, note the proportional decrease in amplitude of both components of the pattern.

Figure 6:
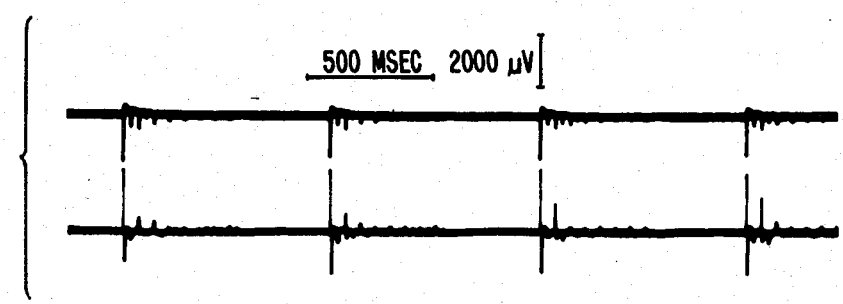
FIG. 6—Continuation of FIG. 5.

FIG. 6 is a continuation of FIG. 5. Note the increase in the amplitude of FAP on the upper trace. The CEEP pattern or the lower trace remains unchanged.

Figure 7:
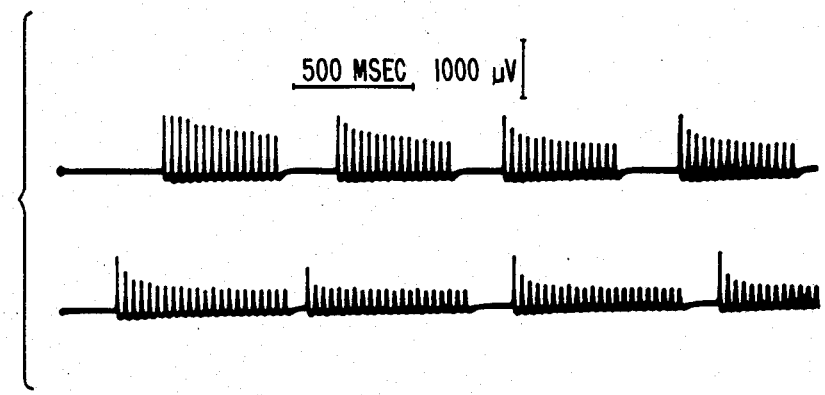
FIG. 7—Squamous cancer of the lung. Variations of the CEEP morphology related to the length of the stimulation trains.

FIG. 7 shows the EMG of a frog left gastrocnemius after injection with the serum of a patient with squamous cancer of the lung. 700 msec (upper) and 1000 msec (lower) trains of 0.05 msec at 24 c/5 stimulation are shown. Note on the upper trace the CEEP elicitation of moderate resolution. Note on the lower trace the increase in Ca E Ac/train ratio proportional to the train length.

FIGS. 8A-8D show alternative forms of innervation patterns of multiple innervated muscle.

Figure 9:
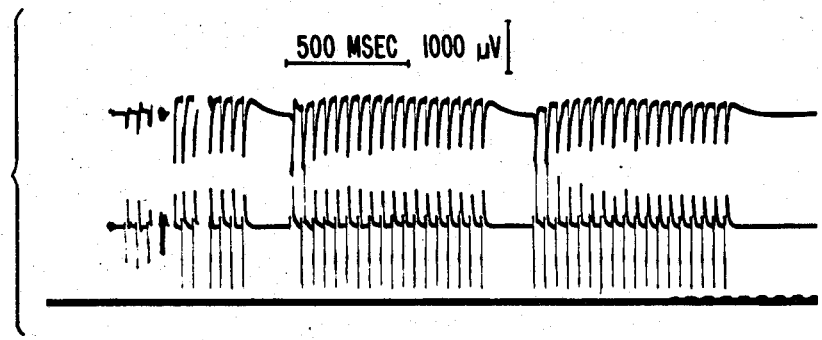
FIG. 9—Examples of CEEP elicited by serum of patient with thyroid carcinoma.
Figure 8A:
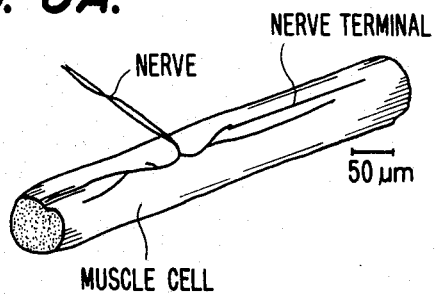
FIGS. 8A-8D—Patterns of frog's neuromuscular junction.
Figure 8B:
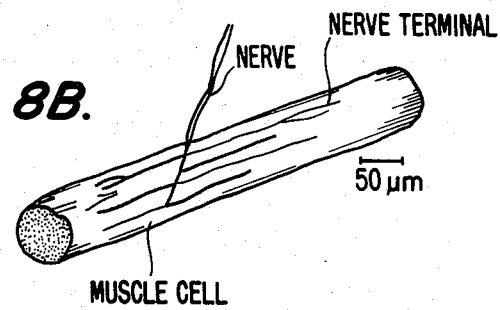
Figure 8C:
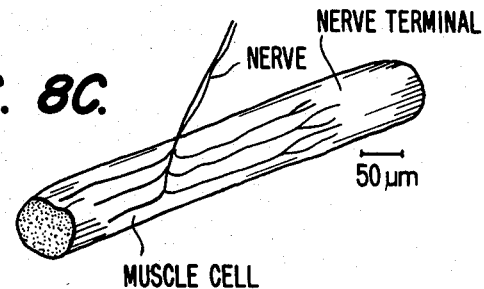
Figure 8D:
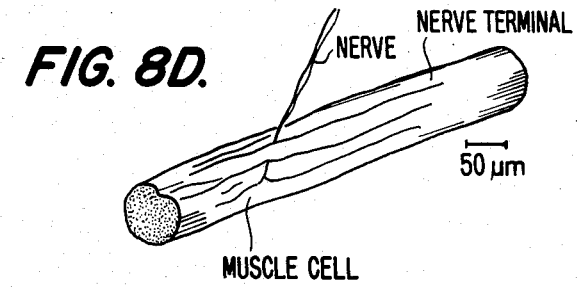

FIG. 9 shows the EMG of a frog gastocnemius after injection with the serum of a 40 year old woman with thyroid carcinoma. 1000 msec trains of 0.05 msec are shown. Both electrodes were applied to the same muscle, slightly separated. The figure shows the elicitation of CEEP in progress, as well as sawtooth and staircase phenomena.

Figure 10:
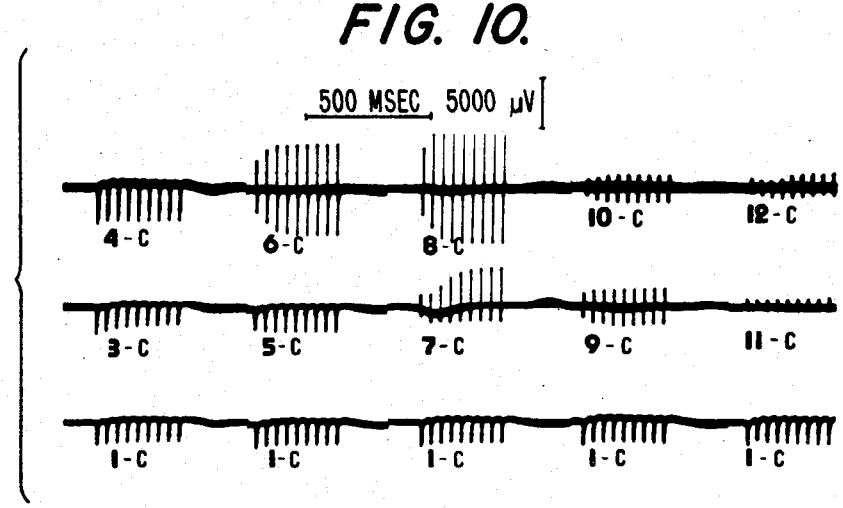
FIG. 10—Multi-electrode recording of CEEP by monopolar leads.

FIG. 10 shows the monopolor multielectrode record explored along the long muscle axis of the normal frog gastrocnemius. 500 msec trains of 0.05 msec at 18 c/s stimulation are shown. The leads are labelled. Note the electrogenic focus, spindle-like, spreading decrementally between leads 6 and 10 and the steep transition from the anterior leads (1 to 5).

Figure 11:
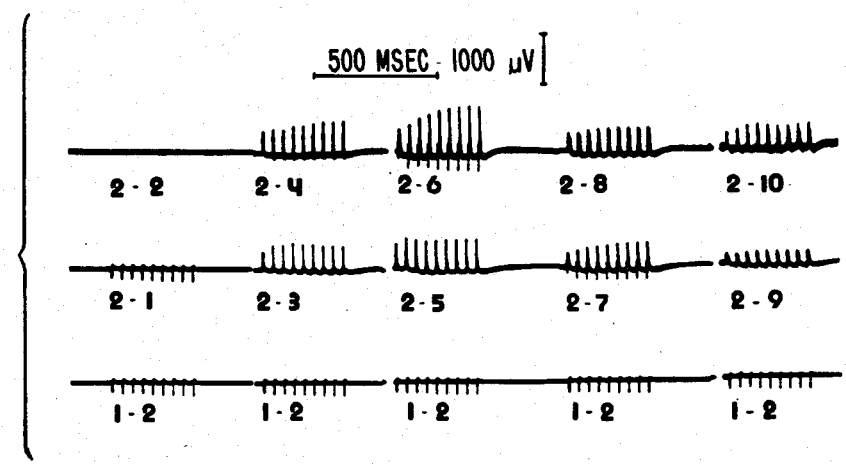
FIG. 11—Multi-electrode recording of CEEP by bipolar leads.

FIG. 11 is similar to FIG. 9 except that the bipolar multielectrode axis record is shown. Note the electrogenic axis focus with the maximum amplitude located in lead 6.

Figure 12:
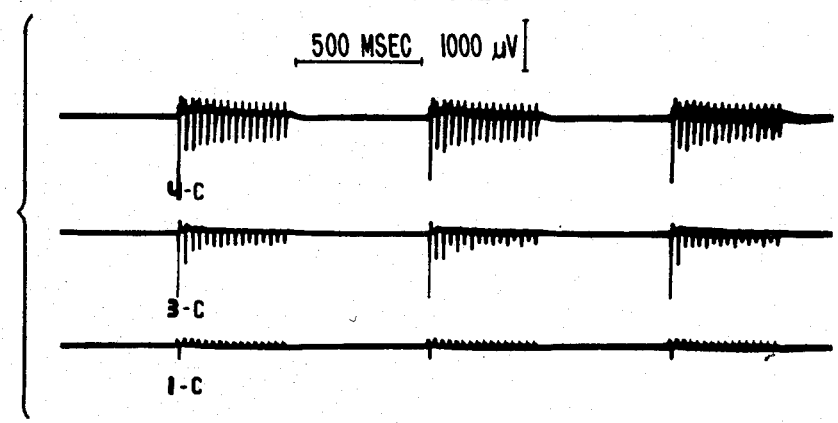
FIG. 12—Independent electrical foci on the same muscle recorded by multi-electrode technique.

FIG. 12 shows the EMG of a toad right gastrocnemius after injection with the serum of a 12 year old child with AML. 700 msec trains of 0.05 ec at 28 c/s stimulation employing monopolar multielectrode recording in the muscle's long axis are shown. This Figure is evidence for the existence of two independent electrogenic foci. Note the identical Ca E Ac in two distinct derivations (A, B) together with different AP train amplitude. The leads are labelled.

Figure 13:
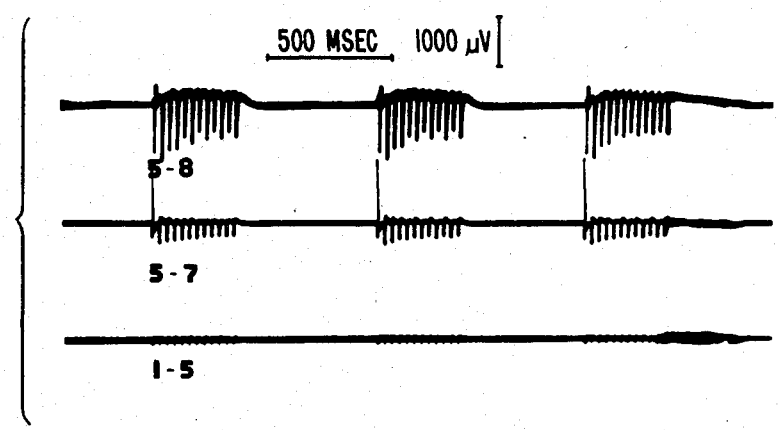
FIG. 13—Volume conductor analysis of the CEEP of a gastric cancer patient.

FIG. 13 shows the bipolar multielectrode exploration of a toad gastrocnemius after injection with the serum of a gastric cancer patient. 500 msec trains of 0.05 msec at 24 c/s stimulation are shown. The leads are labelled. Note that moving the common electrode distally (5) brings about a clear phase opposition CEEP on the second channel and suppression of electrical activity on the first channel (lower trace).

Figure 14:
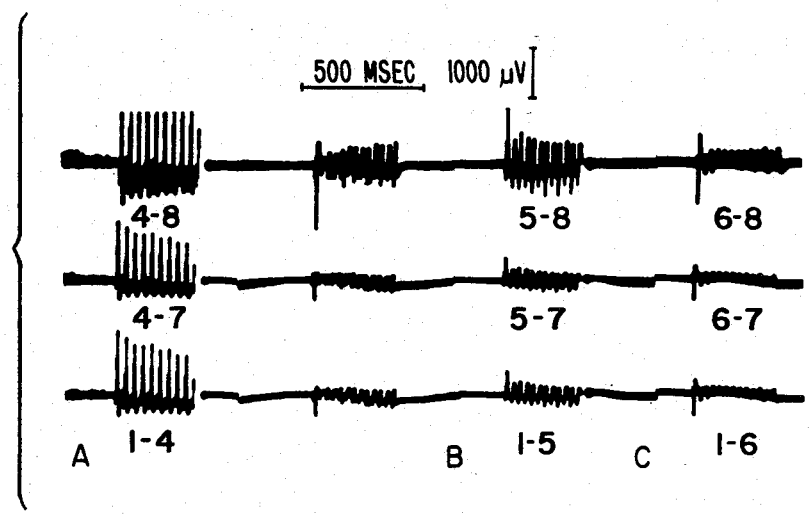
FIG. 14—Volume conductor exploration of the CEEP in a malignant melanoma patient.

FIG. 14 shows the results of bipolar multielectrode exploration of a toad gastrocnemius after injection with the serum of a patient with malignant melanoblastoma. 500 msec trains of 0.05 msec at 24 c/s stimulation are shown. The leads are labelled. Note that the switching of the reference lead between 1 and 8 elicits Ca E Ac successively in upward deflection, downward deflection, and biphasic. The reference standard is at the beginning.

The amphibia were chosen because they present a combination of advantages which make this model very suitable for this purpose. Firstly, they have the characteristic of the central nervous system common to all the phylum of the vertebrates including the superiors; secondly, they have a neuromuscular organization based mainly on multiple innervation of the muscle; and thirdly the gap between the warm-blooded vertebrates and the poikilotherms makes it possible to use the latter as a biological screen of the changes induced in the former. Other vertebrates having multiple innervated muscle may also be used.

The neurophysiological method used takes advantage of the fact that the scattered neuromuscular junction of the frog is formed by a large number of synaptic units the functional potentials of which are not identical. By an adequately prolonged stimulation, it is possible to inactivate part of these synaptic units and to lower the functional safety margin of the others. By this procedure, the sensitivity of the neuromuscular preparation to a toxic agent which is otherwise inefficient, is greatly increased and induced effects become detectable using a suitable EMG procedure.

The detection of the toxic effect of the cancer serum is preferably done on adult amphibia, typically toads or frogs, at room temperature, immobilized by pins on a cork table. The stimulating electrodes are placed on the upper nervous formations of the animal in order to obtain a physiological stimulation of the motorneurons which is further transmitted to the muscle by the large fast-conducting fibers. The evoked muscular action potentials of the gastocnemius muscle of the animal in vivo and in situ are recorded by coaxial electrodes and displayed on the screen of a multichannel electromyograph. The procedure may of course be applied to other multiple innervated muscles of lower sensitivity.

The stimuli are delivered by a neurostimulator and are adjusted to a supraliminary intensity at the shortest time of stimulation possible, which is usually about 0.5 msc. The frequency of stimulation is typically about 1 c/s and after approximately 10 minutes of stimulation at this rate the slow injection of about 0.5-1 cc of serum of the patient to be checked is started typically in the dorsal lymphatic sack of the amphibian. The injection is continued slowly for another five minutes maintaining the 1 c/s neurostimulation for the whole time of the injection.

After the serum injection has been accomplished the presence and the effect of the Cancer Humoral Factor is sought by the elicitation of the EMG activity by trains of stimuli which vary in frequency and length. The stimulation of the neuromuscular amphibian preparation by the procedure described above elicits trains of motor unit potentials equal in shape and size, maintained without modifications for long periods of stimulation. FIG. 1 shows the record of the physiological pattern which appears when the frog has been injected with control serum taken from normal individuals or from individuals with various conditions other than cancer.

The evoked electromyographical pattern changes in the case of injection of cancer serum, and instead of the pattern of equal size potentials, there appears gradually an EMG patern essentially pathognomonic for the presence of a specific cancer factor. The mechanism of the production of this pattern is clarified below. The main characteristics of the pattern, is a high amplitude of the first motor unit potential of the train followed by a train of the rest of the action potentials, of low amplitude and the same size. (See FIG. 2)

The pattern described above may be subject to a certain number of variations with respect to its morphology, which may be monophasic or biphasic (FIGS. 3 and 4), or in the ratio of differentiation between the First Cancer Accident (F Ca A) and the rest of the train, which may be high or low, or finally in the phase characteristic of the EMG pattern, where the F Ca A may be in the same phase with the rest of the train or in opposition or phase in various degrees (FIGS. 5, 6 and 7).

The invention of an appropriate methodology for the elicitation of the Cancer Electromyographically Evoked Pattern (CEEP) relies on the specific innervation which characterizes the amphibian muscle. The neuromuscular junction of the amphibian muscle is formed by a great number of synaptic units of varying functional value. The prolonged 1 c/s stimulation of the supraspinal formations of the animal consumes a part of the neurotransmitter reserve and the preparation functions with a lower safety margin. If, at this stage, the synaptic units which function just liminally are affected by a toxic factor, which in this case is the cancer humoral factor, and if this inactivation involves selectively only a number of synaptic units then a situation is created where the motor unit potential produced by a population of synaptic units which have a slower recovery time will form the high amplitude F Ca A, whereas the fast recovery of a few synaptic units is responsible for the repetitive low action potentials of the rest of the train.

The prototype of the multiple innervation of the amphibian muscle has already been described in general lines by other authors. In conformity with the electromyographical results of this invention it is found that the real innervation pattern is more extended than has been described and takes one of the alternative forms proposed in FIG. 8.

The proposed mechanism of the formation of CEEP is electrically confirmed by multielectrode investigation in the long axis of the muscle. The record in FIGS. 9, 10 and 12 shows that in the course of the elicitation procedure and under the effect of cancer patient serum the neuromuscular junction of the frog presents two or more different electrogenic foci, triggering independently and having a different morphological expression. The investigations performed in bipolar as well as in monopolar recording show similar resuls and the differences in amplitude and morphology are due only to the difference in the method of recording (FIGS. 10 and 11). The existence of various molecular forms of the choline acetyl transferase or (ChAT) isomers is well-established although their biochemical identification is very difficult in the central nervous system and impossible in the peripheral muscular synapse. It has been confirmed that the difference in the functional value of the synaptic units is due to their differing content of neurotransmitter. The synthesis of acetyl choline (ACh) is ultimately regulated by the transferase involved in the ACh metabolism. The variation in the functional value of the synaptic unit and the synaptic vesicles content of ACh may be affected by an impairment in the synthesis of ACh as a consequence of the inhibitory action exerted by the cancer humoral factor on the transferase. The morphology of the CEEP is explained by the inhibition of some of the active forms of the ChAT (target isomers) only, while other isomeric forms of ChAT remain unaffected or are even are activated.

The present electromyographical method of assessment of neuromuscular junction allows therefore, the possibility of identifying one or more cancer accompanying products by a specific action of the product on the various ChAT isomers. Variations in the parameters of stimulation may induce modifications in the CEEP characteristic for the inhibition and/or activation of some ChAT isomers by a specific cancerous serum (see FIGS. 12, 13 and 14). The neuromuscular junction of the frog and toads have proved to be a very sensitive mirror which reacts by functional changes to pathological biochemical modifications of the blood to be tested.

The assessment of the functional effects of the accompanying cancer products introduces a new criterion in cancer research. This criterion has a diagnostic importance by itself and also may open a new line of research in immunology by the use in immunological procedures of identified and isolated cancer products which have functional activity.

Obviously, this invention may be practiced within the scope of the approved claims in other manners than that described specifically in this specification. Accordingly, the invention should be interpreted broadly within the scope of these claims.

What is claimed is:

1. A method of identifying cancer in a suspected cancer patient, comprising the steps of:
electrically stimulating the neuromuscular junction of a multiple-innervated muscle of a vertebrate;

injecting said vertebrate with the serum of a suspected cancer patient while continuing said electrical stimulating step;

varying the frequency, intensity and duration of said stimulation to obtain an electromyographical pattern determining the presence or absence of cancer electromyographically evoked activity;

whereby the presence of said cancer electromyographically evoked activity is a positive indication of the presence in the patient of a serum factor only produced when the patient has a cancerous condition.

2. The method of claim 1 wherein said vertebrate is an amphibian.

3. The method of claim 2 wherein said neuromuscular junction is that of the gastrocnemius muscle.

4. The method of claim 2 wherein said initial stimulation is of about 0.05 msec duration and a frequency of about 1 c/s and comprising continuing said initial stimulation for about 10 minutes prior to said injection step.

5. The method of claim 4 comprising injecting about 0.5-1 cc of said serum into the dorsal lymphatic sack of said amphibian injected at an approximately constant rate over about five minutes time.

6. The method of claim 5 wherein said amphibian is selected from the group consisting of frogs and toads.

7. A method of performing a bioassay of a cancer humoral factor in a serum, comprising the steps of:

electrically stimulating the neuromuscular junction of a multiple-innervated muscle of a vertebrate;

injecting said vertebrate with a sample of said serum of while continuing said electrical stimulating step;

varying the frequency, intensity and duration of said stimulation to obtain an electromyographical pattern;

determining the presence or absence of cancer electromyographically evoked activity;

whereby the presence of said cancer electromyographically evoked activity is a positive indication of the presence in the serum of a cancer humoral factor.

* * * * *